United States Patent [19]
Kelly

[11] 4,048,193
[45] Sept. 13, 1977

[54] PROCESS FOR BICYCLIC LACTONE DIALS

[75] Inventor: Robert C. Kelly, Kalamazoo, Mich.

[73] Assignee: The Upjohn Company, Kalamazoo, Mich.

[21] Appl. No.: 583,556

[22] Filed: June 4, 1975

Related U.S. Application Data

[62] Division of Ser. No. 374,349, June 28, 1973, Pat. No. 3,904,648.

[51] Int. Cl.$^2$ .......................................... C07D 317/30
[52] U.S. Cl. ..................... 260/343.3 R; 260/340.9 P
[58] Field of Search ................ 260/343,3 P, 343.3 TR

[56] References Cited
U.S. PATENT DOCUMENTS 3,953,473 4/1976 Van Rheenen ................ 250/343.3 P

*Primary Examiner*—Paul J. Killos
*Attorney, Agent, or Firm*—Morris L. Nielsen

[57] ABSTRACT

Process for preparing bicyclic lactone diols of the formula

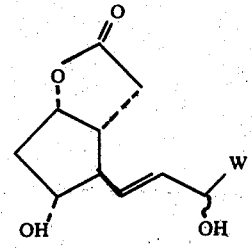

wherein W is 1-pentyl, cis 1-pent-2-enyl, or 1-pent-2-ynyl by way of a cyclic ortho ester; and the intermediates prepared therein. The diols are useful intermediates in preparing prostaglandins having pharmacological utility.

6 Claims, No Drawings

PROCESS FOR BICYCLIC LACTONE DIALS

CROSS REFERENCE TO RELATED APPLICATIONS

This is a division of application Ser. No. 374,349, filed June 28, 1973, now issued as U.S. Pat. No. 3,904,648.

BACKGROUND OF THE INVENTION

This invention relates to intermediates useful in the preparation of prostaglandins and to a process for preparing them.

Each of the known prostaglandins is a derivative of prostanoic acid which has the following structure and atom numbering:

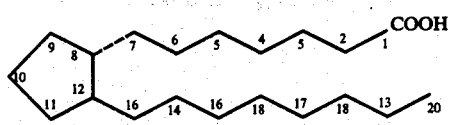

A systematic name for prostanoic acid is 7-[(2β-octyl)-cyclopent-1α-yl]heptanoic acid.

Prostaglandin $E_2$, "$PGE_2$", has the following structure:

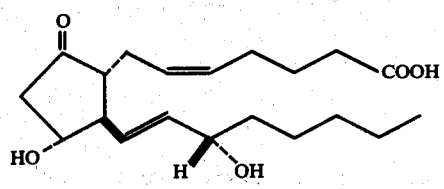

Prostaglandin $F_{2\alpha}$, "$PGF_{2\alpha}$", has the following structure:

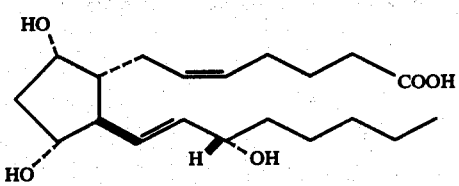

Prostaglandin $F_{2\beta}$, "$PGF_{2\beta}$", has the following structure:

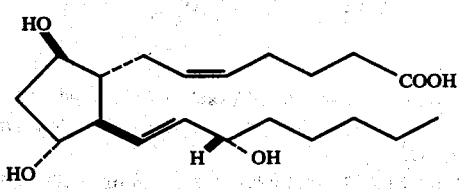

The prostaglandin formulas mentioned above each have several centers of asymmetry. Each formula represents a molecule of the particular optically active form of the prostaglandin obtained from certain mammalian tissues, for example, sheep vesicular glands, swine lung, and human seminal plasma, or by reduction or dehydration of a prostaglandin so obtained. See, for example, Bergstrom et al., Pharmacol. Rev. 20, 1 (1968), and references cited therein. The mirror image of each formula represents a molecule of the other enantiomeric form of that prostaglandin. The racemic form of the prostaglandins consists of equal numbers of two types of molecules, one represented by one of the above formulas and the other represented by the mirror image of that formula. Thus, both formulas are needed to define a racemic prostaglandin. See Nature 212, 38 (1966) for discussion of the stereochemistry of the prostaglandins.

In the formulas above, as well as in the formulas given hereinafter, broken line attachments to the cyclopentane ring indicate substituents in alpha configuration, i.e., below the plane of the cyclopentane ring. Heavy solid line attachments to the cyclopentane ring indicate substituents in beta configuration, i.e., above the plane of the cyclopentane ring. In the formulas above, the hydroxyl attachment to carbon 15 is in the alpha configuration, as indicated by the broken line. In formulas below, this convention is also used for intermediates having hydroxyl substituted at the corresponding position on the side chain. A wavy line ∼ indicates optional attachment to carbon 15 in either alpha or beta configuration.

The various optically active and racemic prostaglandins and their alkyl esters are useful for various pharmacological purposes. With particular regard to $PGF_{2\alpha}$ see, for example, Bergstrom et al., Pharmacol. Rev. 20, 1 (1968), and references cited therein, Wiqvist et al., The Lancet, 889 (1970), and Karim et al., J. Obstet. Gynaec. Brit. Cwlth., 76, 769 (1969). As to the other prostaglandins, see, for example, Ramwell et al., Nature 221, 1251 (1969).

Previously, the preparation of an intermediate bicyclic lactone diol of the formula

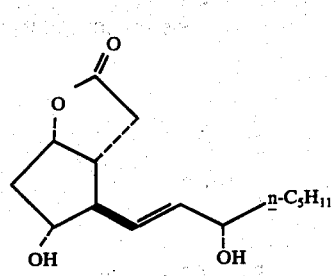

was reported by E. J. Corey et al., J. Am. Chem. Soc. 91, 5675 (1969), and later disclosed in an optically active form by E. J. Corey et al., J. Am. Chem. Soc. 92, 397 (1970). Conversion of this intermediate to $PGE_2$ and $PGE_{2\alpha}$, either in racemic (di-) or optically active form, was disclosed in those publications.

SUMMARY OF THE INVENTION

It is the purpose of this invention to provide novel intermediates useful in the preparation of prostaglandins commercially in substantial amount, with high purity, and at reasonable cost. It is a further purpose to provide processes for preparing these intermediates and for utilizing them.

Thus there is provided an optically active compound of the formula

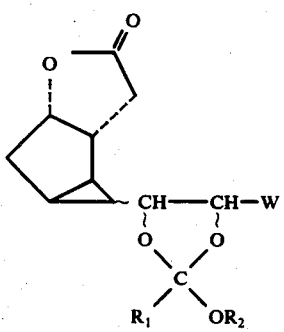

or a racemic compound of that formula and the mirror image thereof, wherein $R_1$ is hydrogen, alkyl of 1 to 19 carbon atoms, inclusive, aralkyl of 7 to 12 carbon atoms, inclusive, substituted with 0 to 3 halo atoms; $R_2$ is methyl or ethyl; W is 1-pentyl, cis 1-pent-2-enyl, or 1-pent-2-ynyl; and ~ indicates attachment of the moiety to the side chain in alpha or beta configuration.

This invention likewise provides a process by which cyclic ortho ester II is prepared and subsequently transformed into a bicyclic lactone diol of the formula

III

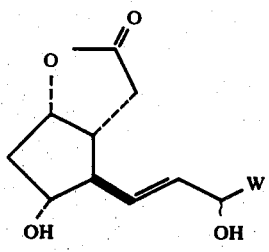

Thus there is provided a process for preparing an optically active bicyclic lactone diol of the formula

III

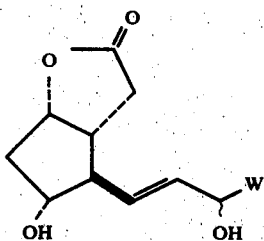

or a racemic compound of that formula and the mirror image thereof, wherein W is 1-pentyl, cis 1-pent-2-enyl, or 1-pent-2-ynyl, and ~ indicates attachment of the hydroxyl to the side chain in alpha or beta configuration, which comprises the steps of a. reacting an optically active tricyclic lactone glycol of the formula

IV

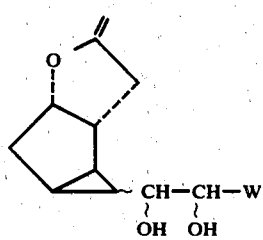

or a racemic compound of that formula and the mirror image thereof, wherein W is as defined above and ~ indicates attachment of the moiety to the cyclopropane ring in exo and endo configuration and to the side chain in alpha or beta configuration, with an ortho ester of the formula

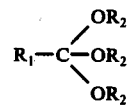

wherein $R_1$ is hydrogen, alkyl of 1 to 19 carbon atoms, inclusive, or aralkyl of 7 to 12 carbon atoms, inclusive, substituted with zero to 3 halo atoms; and $R_2$ is methyl or ethyl, to form an optically active cyclic ortho ester of the formula

II

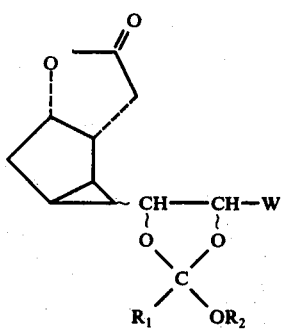

or a racemic compound of that formula and the mirror image thereof, wherein $R_1$, $R_2$, W, and ~ are as defined above;

b. reacting said cyclic ortho ester with formic acid to form an optically active diol diester of the formula

V

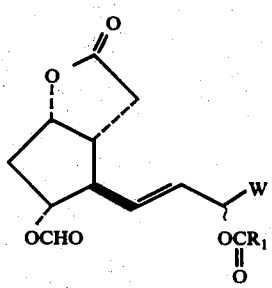

or a racemic compound of that formula and the mirror image thereof, wherein $R_1$, W, and ~ are as defined above; and c. replacing the acyl groups of said diol diester with hydrogen.

Previously, steps by which glycol IV is transformed to diol III were disclosed in my U.S. Pat. No. 3,711,515, issued Jan. 16, 1973. For example, the glycol hydrogen atoms of glycol IV are replaced by an alkylsulfonyl group and the product subjected to hydrolysis. Alternatively the mixed isomeric glycols IV are transformed to the diformate of bicyclic lactone diol III in 100% formic acid and thence to diol III, e.g. with potassium bicarbonate in methanol.

It has now been found that the transformation of glycol IV to diol III can be accomplished with stereospecificity and consequently higher yield of the desired isomer by way of a cyclic ortho ester. Reference to Chart A, steps (a), (b), and (c), will make clear the process by which this is accomplished. In Chart A, $R_1$ is hydrogen, alkyl of 1 to 19 carbon atoms, inclusive, or aralkyl of 7 to 12 carbon atoms, inclusive, substituted with zero to 3 halo atoms; $R_2$ is methyl or ethyl; W is as defined herein, i.e. 1-pentyl, cis 1-pent-2-enyl, or 1-pent-2-ynyl; and ~ indicates attachment of the moiety to the side chain in alpha or beta configuration.

In step (a) of Chart A, tricyclic lactone glycol IV is transformed to cyclic ortho ester II. Glycol IV exists in two erythro and two threo forms:

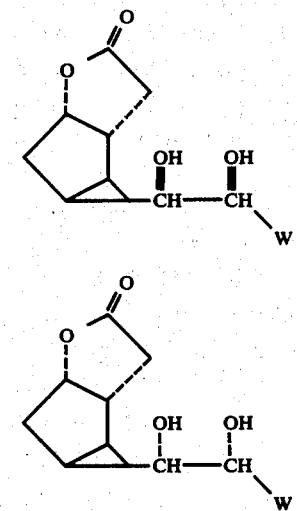

CHART A

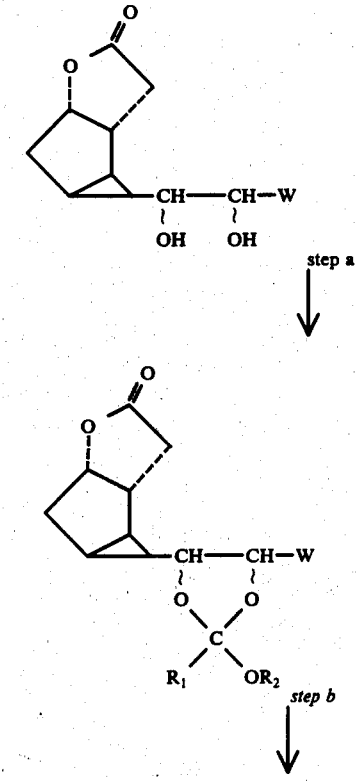

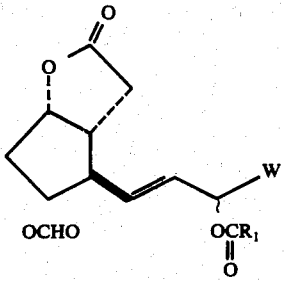

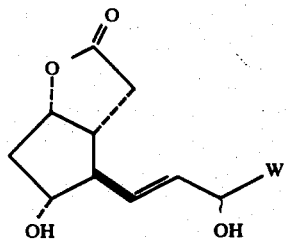

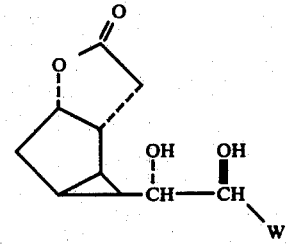

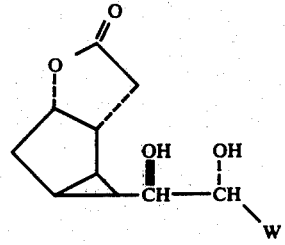

These various glycols are available, for example by hydroxylation of a corresponding alkene or alkenyne as disclosed in the above-referenced U.S. Pat. No. 3,711,515 to yield the 1-pentyl or 1-pent-2-ynyl compounds. When the cis-1-pent-2-enyl compounds are desired, the —C≡C— moiety of the 1-pent-2-ynyl compounds is reduced to —CH=CH— after the hydroxylation step. Those sections of U.S. Pat. No. 3,711,515 relating to the preparation and separation of the respective glycols, particularly Examples 1-6, and 13-17, are incorporated by reference herein.

The four glycols IVa, IVb, IVc, and IVd wherein W is 1-pentyl are named respectively as follows:

endo-6-(IR,2S-dihydroxyheptyl)-exo-3-hydroxybicyclo[3.1.0]hexan-exo-2-acetic acid, γ-lactone,
endo-6-(IS,2R-dihydroxyheptyl)-exo-3-hyroxybicyclo[3.1.0]hexan-exo-2-acetic acid, γ-lactone,
endo-6-(IS,2S-dihydroxyheptyl)-exo-3-hydroxybicyclo[3.1.0]hexan-exo-2-acetic acid, γ-lactone, and
endo-6-(IR,2R-dihydroxyheptyl)-exo-3-hydroxybicyclo[3.1.0]hexan-exo-2-acetic acid, γ-lactone.

For a discussion of the "R" and "S" nomenclature see, for example, R. S. Chan, J. Chem. Ed. 41, 116 (1964). Note that the designation "2S" herein refers to the S configuration of C-2, the second carbon in the side chain counting from the ring.

For the purposes of this invention according to Chart A, when the 3S formula-III diol is desired, corresponding to a 15S final product $PGF_{2\alpha}$, either the formula-IV$a$ or the formula-IV$c$ 2S glycol is used as the starting material. The "S" configuration at the latent C-15 position is preserved throughout the transformations of steps (a), (b), and (c) of Chart A. Likewise, when the 3R formula-III diol is desired, either the formula-IV$b$ or the formula-IV$d$ 2R glycol is used.

Referring to Chart A, the formula-II cyclic ortho ester is obtained in step $a$ by reaction of glycol IV with an ortho ester of the formula

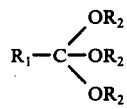

wherein $R_1$ and $R_2$ are as defined above. The reaction goes smoothly in a temperature range of $-50°$ C. to $+100°$ C., although for convenience $0°$ C. to $+50°$ C. is generally preferred. From 1.5 to 10 molar equivalents of the ortho ester are employed, together with an acid catalyst. The amount of the catalyst is usually a small fraction of the weight of the glycol, say 1%, and typical catalysts include pyridine hydrochloride, formic acid, hydrogen chloride, p-toluenesulfonic acid, trichloroacetic acid, or trifluoroacetic acid. The reaction is preferably run in a solvent, for example benzene, dichloromethane, ethyl acetate, or diethyl ether. It is generally completed within a few minutes and is conveniently followed by TLC (thin layer chromatography on basic silica gel plates).

The ortho ester reagents are known in the art or readily available by methods known in the art. See for example S. M. McElvain et al., J. Am. Chem. Soc. 64, 1925 (1942), starting with an appropriate nitrile. Examples of useful ortho esters include:

trimethyl orthoformate,
triethyl orthoacetate,
triethyl orthopropionate,
trimethyl orthobutyrate,
triethyl orthovalerate,
trimethyl orthooctanoate,
trimethyl orthophenylacetate, and
trimethyl ortho (2,4-dichlorophenyl)acetate.

Preferred are those ortho esters wherein $R_1$ is alkyl of 1 to 7 carbon atoms, especially preferred are those wherein $R_1$ is alkyl of 1 to 4.

The formula-V diester is obtained in step (b) by reaction of the formula-II cyclic ortho ester with anhydrous formic acid. By "anhydrous formic acid" is meant that it contains not more than 0.5% water. The reaction is run with an excess of formic acid, which may itself serve as the solvent for the reaction. Solvents may be present, for example dichloromethane, benzene, or diethyl ether, usually not over 20% by volume of the formic acid. There may also be present organic acid anhydrides, for example acetic anhydride, or alkyl orthoesters, for example trimethyl orthoformate, which are useful as drying agents for the formic acid. Although the reaction proceeds over a wide range of temperatures, it is conveniently run at about $20°$–$30°$ C. and is usually completed within about 10 minutes. Thereafter the product is recovered and purified if desired by methods known in the art.

The formula-III diol is obtained in step $c$ by alcoholysis of the formula-V diester in the presence of a base. Examples of the base are sodium or potassium carbonate or sodium or potassium alkoxides including methoxides or ethoxides. The reaction is conveniently run in an excess of the solvolysis reagent, for example methanol or ethanol. The temperature range is from $-50°$ C. to $100°$ C. The time for completion of the reaction varies with the nature of $R_1$ and the base, proceeding in the case of alkali carbonates in a few minutes when $R_1$ is hydrogen but taking up to several hours when $R_1$ is ethyl, for example.

Referring to Chart B, there are shown alternate routes from diester V$\alpha$ to diol III$\alpha$. In step (a), diester V$\alpha$ is hydrolyzed to triol acid VII, opening the lactone. The hydrolysis occurs in the presence of a base, such as sodium or potassium carbonate or hydroxide. With alkali carbonates, a solvent containing water, for example methanol-water or tetrahydrofuran-water, is used whereas with alkali hydroxides no water need be added.

CHART B

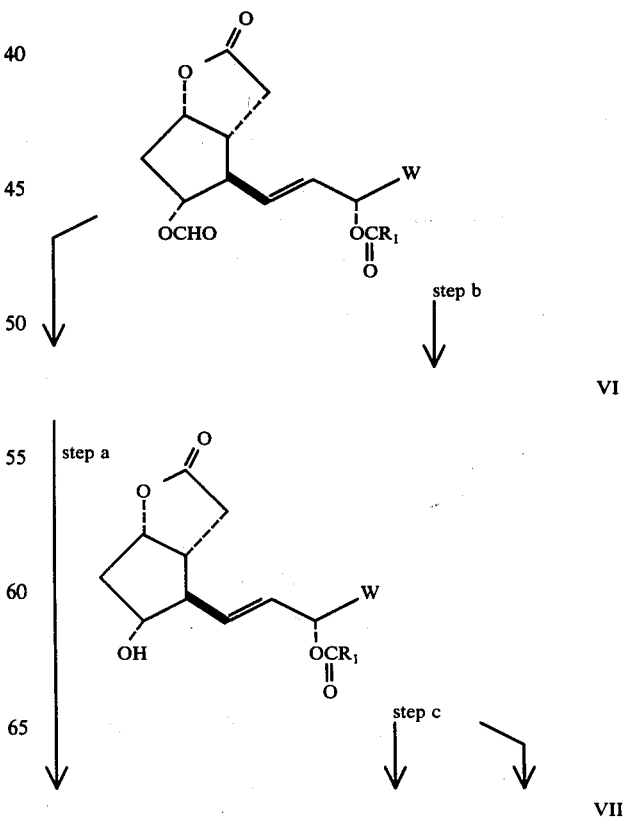

-continued
CHART B

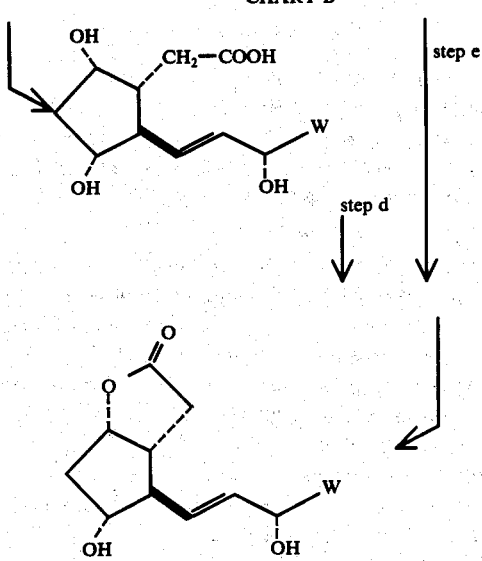

IIIa

Thereafter, triol acid VII is transformed to diol IIIa in step (d) by lactonization in the presence of an acid, for example pyridine hydrochloride, hydrogen chloride, p-toluenesulfonic acid, acetic acid, and the like in a solvent such as dichloromethane, benzene, toluene or chloroform at reflux temperature. At temperatures above 100° C., for example in refluxing toluene, the lactonization proceeds without an acid catalyst. The formation of the lactone is conveniently followed by TLC.

Alternatively, when $R_1$ is not hydrogen, a monoester of formula VI is obtained as in step (b) by preferential alcoholysis of the formyl group of diester Va. For this purpose methanolysis with potassium bicarbonate or potassium carbonate is useful. This intermediate VI is useful for either preparing the triol acid VII in step (c), by alkaline hydrolysis discussed above, or by alkaline alcoholysis for a sufficient time to remove the

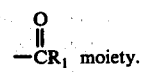
moiety.

The steps shown in Chart B are directed toward 3S diols of formula IIIa. By starting with 3R diesters corresponding to formula Va, wherein the attachment to C-3 is in the beta configuration, the same chemical transformations yield 3R diols corresponding to formula IIIa.

As stated above the 2R glycols of formula IVb or -IVd by the steps of Chart A, yield the 3R formula-III diol. When the 3S formula-III diol is desired, there is available a procedure for epimerizing either of the 2R glycols to 2S glycols.

In Chart C are shown the steps by which glycol VIII is epimerized to glycol XII. In glycol VIII the 2-hydroxy is in the R configuration and the 1-hydroxy is in either R or S configuration. In glycol XII the 2-hydroxy is in th S configuration and the 1-hydroxy is in the same configuration as in VIII. This, in Chart C, ~ indicates attachment of the moiety to the side chain in either alpha or beta configuration. Further, in Chart C, $R_3$ and $R_4$ are alkyl of 1 to 10 carbon atoms, inclusive aralkyl of 7 to 12 carbon atoms, inclusive, phenyl or phenyl substituted with 1 or 2 halo or alkyl groups of 1 to 4 carbon atoms, inclusive. If $R_3$ is alkyl, it is preferably of 3 or more carbon atoms. $R_3$ and $R_4$ may be the same or different. For example, $R_3$ may be n-butyl when $R_4$ is methyl. In formula XI, one of E and M is hydrogen and the other is an acyl group of the formula —C-(O)—$R_4$.

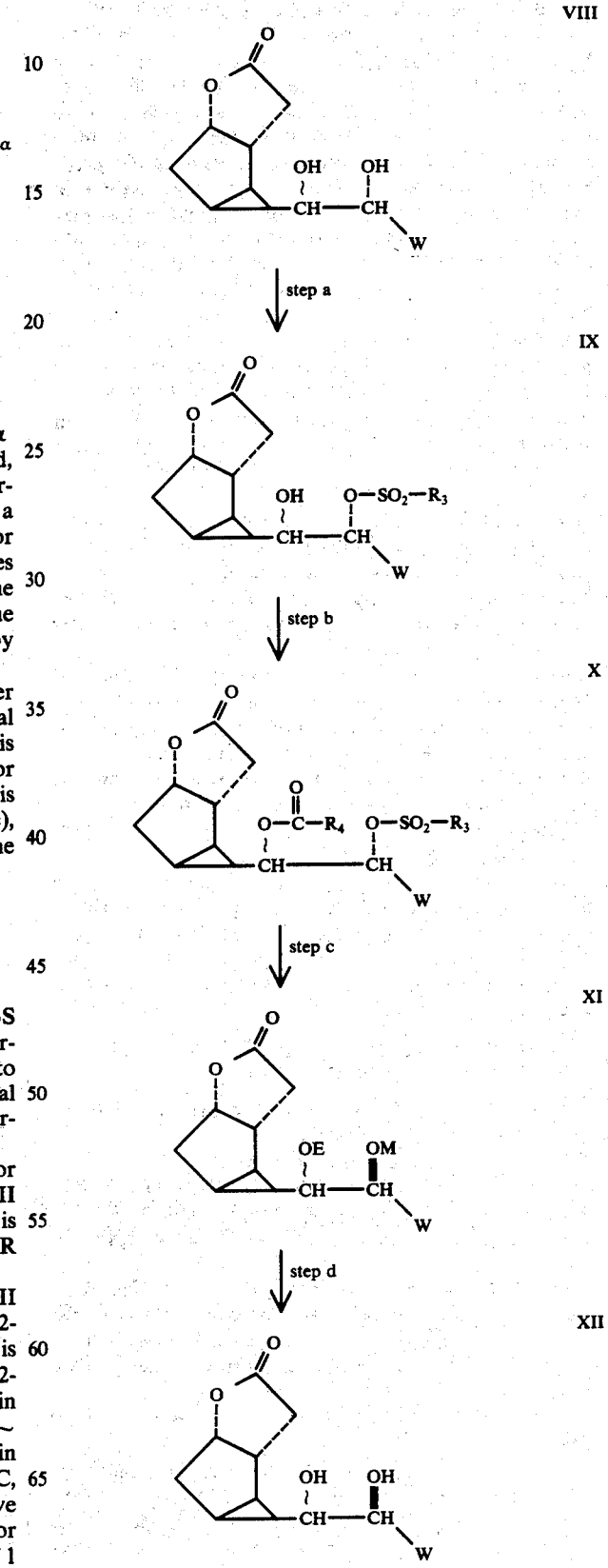

It will be recognized that formula VIII includes both glycol IVb and glycol IVd above, obtained by the processes disclosed in U.S. Pat. No. 3,711,515 and that formula XII includes both glycol IVa and glycol IVc, useful for the preparation of diols III and IIIα by the steps of Charts A and B.

Continuing with Chart C, the formula-IX sulfonate is obtained in step a by reaction of glycol VIII with a sulfonyl chloride of the formula $R_3$—$SO_2$—Cl wherein $R_3$ is as above defined. To achieve selective activation of the C-2 hydroxyl it is preferred that the $R_3$ group contain 3 or more carbon atoms, for example n-butyl, phenyl, or p-tolyl. The reaction is done with about 3 molar equivalents of the sulfonyl chloride in the presence of a tertiary amine. Preferably a solvent system of diethyl ether or dichloromethane containing the tertiary amine, for example pyridine in about 33% by volume, is used. The reaction is run preferably at about 0° C. and is generally complete within 5 days as shown by TLC.

Diester X is obtained is step (b) by reaction of sulfonate IX with an acid anhydride of the formula $(R_4)_2O$ or acyl halide of the formula $R_4$Hal where Hal is bromo or chloro. Particularly useful for this purpose are acylating agents in which $R_4$ is alkyl of 1 to 3 carbon atoms, inclusive, for example acetic anhydride or propionic anhydride.

Mixed monoesters XI are obtained in step (c) by treatment of diester X with 90% aqueous acetic acid containing 4 molar equivalents of sodium acetate at 90° C. The reaction is generally completed in a few hours. See R. B. Woodward et al., J. Am. Chem. Soc. 80, 209 (1958).

Finally, glycol XII is obtained in step (d) by removal of the acyl group. This is preferably done in absolute methanol with sodium methoxide, followed by quenching in aqueous acetic acid. Alternatively, use of 2 N. sodium hydroxide in methanol-water results in simultaneous lactone-opening and hydrolysis of the acyl group. Acidification to pH 3 restores the lactone ring and permits recovery of glycol XII.

The steps shown in Chart C are directed toward 2S glycols of formula XII. By starting instead, with 2S glycols corresponding to formula VIII but with S configuration at C-2, the same chemical transformations yield 2R glycols corresponding to formula XII but with R configuration at C-2.

DESCRIPTION OF THE PREFERRED EMBODIMENTS

The invention is further illustrated by, but not limited to, the following examples.

All temperatures are in degrees centigrade.

Infrared absorption spectra are recorded on a Perkin-Elmer model 421 infrared spectrophotometer. Except when specified otherwise, undiluted (neat) samples are used.

The NMR spectra are recorded on a Varian A-60 spectrophotometer in deuterochloroform solutions with tetramethylsilane as an internal standard (downfield).

"Brine", herein, refers to an aqueous saturated sodium chloride solution.

"Skellysolve B", herein, refers to mixed isomeric hexanes.

"TLC", herein, refers to thin layer chromatography.

Silica gel chromatography, as used herein, is understood to include elution, collection of fractions, and combination of those fractions shown by TLC to contain the desired product free of starting material and impurities.

EXAMPLE 1

Cyclic Ortho Ester of Endo-6-(1R, 2S-dihydroxyheptyl)-exo-3-hydroxybicyclo[3.1.0]hexan-exo-2-acetic Acid, γ-Lactone (Formula II: $R_1$ is hydrogen, $R_2$ is methyl, W is 1-pentyl, CH—O— of C-1 is in R configuration and CH—O— of C-2 is in S configuration)

Refer to Chart A. Glycol IV is obtained by Example 16 of U.S. Pat. No. 3,711,515, using the less polar erythro glycol. A 1-20% solution of the glycol in benzene is treated with trimethyl orthoformate (1.5-10 molar equivalents) and a catalytic amount (1% of the weight of the glycol) of pyridine hydrochloride at about 25° C. The reaction is followed by TLC and is complete in a few minutes. The mixture is concentrated under reduced pressure to yield the formula-II compound, 100% yield, having NMR peaks at 0.7–3.1, 3.39, 3.4–3.8, 3.9–4.5, 4.7–5.1, 5.72, and 5.76 δ.

EXAMPLE 2

Cyclic Ortho Ester of Endo-6-(1R, 2S-dihydroxyheptyl)-exo-3-hydroxybicyclo[3.1.0]hexan-exo-2-acetic Acid, γ-Lactone (Formula II: $R_1$ is methyl, $R_2$ is ethyl, and W is 1-pentyl)

Refer to Chart A. Following the procedure of Example 1 but employing triethyl orthoacetate instead of trimethyl orthoformate, the formula -II title compound is obtained, 100% yield, having $R_f$ 0.77 (TLC on silica gel in 1:1 ethyl acetate-Skellysolve B).

EXAMPLE 3

Cyclic Ortho Ester of Endo-6-(1R, 2S-dihydroxyheptyl)-exo-3-hydroxybicyclo[3.1.0]hexan-exo-2-acetic Acid, γ-Lactone (Formula II: $R_1$ and $R_2$ are ethyl, and W is 1-pentyl)

Refer to Chart A. Following the procedure of Example 1, but employing triethyl orthopropionate instead of trimethyl orthoformate, the formula-II title compound is obtained, 100% yield, having $R_f$ 0.80 (TLC on silica gel in 1:1 ethyl acetate-Skellysolve B).

Following the procedure of Example 3, but replacing the starting formula-IV glycol with the corresponding glycols wherein W is cis 1-pent-2-enyl or 1-pent-2-ynyl (U.S. Pat. No. 3,711,515, especially Example 17), there are obtained the corresponding formula-II cyclic ortho esters namely:

cyclic ortho ester of endo-6-(1R, 2S-dihydroxyhept-4-enyl)-exo-3-hydroxybicyclo[3.1.0]hexan-exo-2-acetic acid, γ-lactone; and cyclic ortho ester of endo-6-(1R, 2S-dihydroxyhept-4-ynyl)-exo-3-hydroxybicyclo[3.1.0]hexan-exo-2-acetic acid, γ-lactone.

Likewise, following the procedures of Examples 3, but employing the corresponding racemic glycols (U.S. Pat. No. 3,711,515) there are obtained the racemic cyclic ortho esters corresponding to formula II.

EXAMPLE 4

3α-(Formyloxy)-5α-hydroxy-2β-[(3S)-3-acetyloxy-trans-1-octenyl]-1α-cyclopentan-acetic Acid, γ-Lactone (Formula V: R₁ methyl, W is 1-pentyl, and ~ is alpha Refer to Chart A. The formula-II cyclic ortho ester (Example 2, 0.26 g.) is treated with 20 volumes of 100% formic acid at about 25° C. The reaction is followed by TLC and is usually complete in 10 min. The reaction mixture is quenched in water or aqueous alkaline bicarbonate solution and extracted with dichloromethane. The organic phase is shaken with 5% aqueous sodium bicarbonate, dried over soidum sulfate, and concentrated under reduced pressure to the formula -V title compound, 90% yield, having NMR peaks at 0.7–1.8, 2.03, 2.0–3.1, 4.7–5.5, 5.5–5.7, 8.04, and 8.09 δ.

EXAMPLE 5

3α-(Formyloxy)-5α-hydroxy-2β-[(3S)-3-propionyloxy-trans-1-octenyl]-1α-cyclopentan-acetic Acid, γ-Lactone (Formula V: R₁ is ethyl, W is 1-pentyl, and ~ is alpha)

Refer to Chart A. Following the procedure of Example 4, the cyclic ortho ester of Example 3 is transformed to the formula-V title compound, 86% yield, having NMR peaks at 0.65–1.9, 2.1–3.1, 4.7–5.5, 5.5–5.7, and 8.05 δ.

Following the procedure of Example 5, but replacing the cyclic ortho ester of that example with the cyclic ortho esters, either optically active or racemic, following Example 3, there are obtained the formula-V diol diesters and the corresponding racemic compounds, including:

3α-(formyloxy)-5α-hydroxyl-2β-[(3S)-3-propionyloxy-trans-1-cis-5-octadienyl]-1α-cyclopentan-acetic acid, γ-lactone; and 3α-(formyloxy)-5α-hydroxy-2β-[(3S)-3-propionyloxy-trans-1-octen-5-ynyl]-1α-cyclopentan-acetic acid, γ-lactone.

EXAMPLE 6

3α,5α-Dihydroxy-2β-[(3S)-3-hydroxy-trans-1-octenyl]-1α-cyclopentan-acetic Acid, γ-Lactone (Formula III: W is 1-pentyl and ~ is alpha)

Refer to Chart A. The formula-V 3S diol diester (Example 4, 1.4 g.) is treated with 10–50 volumes of anhydrous methanol and potassium carbonate (0.17 g.) at about 25° C. The reaction is followed by TLC and if the reaction is not complete in 2 hr. another 0.1 g. of potassium carbonate is added, with stirring continued until the reaction is complete. The formula-III title product is obtained, 96% yield, having infrared absorption bands at 3390, 1760, 1115, 1085, 1035, 970. and 905 cm⁻¹.

EXAMPLE 7

3α,5α-Dihydroxy-2β-[(3S)-3-hydroxy-trans-1-octenyl]-1α-cyclopentan-acetic Acid, γ-Lactone (Formula III: W is 1-pentyl and ~ is alpha)

Following the procedure of Example 6 but replacing the diol diester of that example with the diol diester obtained in Example 5(1.4 g), there is obtained the formula-III title product having the same properties as reported in Example 6.

Following the procedure of Example 7, but replacing the diol diester of that example with the diol diesters, either optically active or racemic, following Example 5, there are obtained the formula-III diols and the corresponding racemic compounds, including:

3α,5α-dihydroxy-2α-[(3S)-3-hydroxy-trans-1-cis-5-octadienyl]-1α-cyclopentan-acetic acid, γ-lactone; and 3α,5α-dihydroxy-2β-[(3S)-3-hydroxy-trans-1-octen-5-ynyl]-1α-cyclopentan-acetic acid, γ-lactone.

EXAMPLE 8

3α,5α-Dihydroxy-2β-[(3R)-3-hydroxy-trans-1-octenyl]-1α-cyclopentan-acetic Acid, γ-Lactone (Formula III: W is 1-pentyl and ~ is beta)

Refer to Chart A.

a. Following the procedure of Example 3 but replacing the less polar erythro glycol of that Example with the more polar erythro glycol having the 1S, 2R configuration (Example 16 of U.S. Pat. No. 3,711,515) there is obtained the cyclic ortho ester of endo-6-(1S, 2R-dihydroxy-heplyl)-exo-3-hydroxybicyclo[3.1.0]hexan-exo-2-acetic Acid, γ-Lactone.

b. Following the procedure of Example 4, the product of step a above is converted to the corresponding formula-V 3R diol diester.

c. Following the procedure of Example 6, the product of step b (1.0 g) is transformed to the formula-III title product, 95% yield, having R_f 0.52 (TLC on silica gel in acetone-dichloromethane (40–60)).

EXAMPLE 9

Triol Acid (Formula VII: W is 1-pentyl)

1. Refer to Charts A and B. The formula-Vα 3S diol diester is first prepared, following steps (a) and (b) of Chart A. The formula-IV 1R, 2S glycol (see Example 1, 1.0 g.) in 5 ml. of benzene is treated with 2.0 ml. of triethyl orthopropionate and the mixture is concentrated under reduced pressure. The residue is taken up in 5 ml. of benzene and treated with 50 μl of a saturated solution of pyridine hydrochloride in dichloromethane. The reaction is shown by TLC to be complete in 40 min. at about 25° C.

Continuing with step (b), the solvent is removed under reduced pressure and the residue treated with 30 ml. of 100% formic acid. After 10 min. the reaction is quenched with about 75 ml. of 5% aqueous sodium hydrogen carbonate solution and the mixture is extracted with dichloromethane. The organic phase is dried over sodium sulfate and concentrated to yield the formula-Vα3S diol diester (R₁ is ethyl and W is n-pentyl) as an oil, 1.46 g.

2. The above product of part 1 is saponified with 15 ml. of methanol and 15 ml. of N. sodium hydroxide for 30 min. at about 25° C. The mixture is concentrated under reduced pressure, acidified to pH 3.5 with M, phosphoric acid, saturated with sodium chloride, and extracted with ethyl acetate. The organic phase is concentrated under reduced pressure to the formula-VII title compound, an oil 1.26 g. which crystallizes. Recrystallization from ethyl acetate gives colorless crystals, m.p. 99°–102° C., 40% yield.

Following the procedure of Example 9, but replacing the formula-V diol diester for that example with the diol diesters, either optically active or racemic, following Example 5, there are obtained the formula-VII triol acids, including those wherein W is cis 1-pent-2-enyl and 1-pent-2-ynyl, and the corresponding racemic products.

EXAMPLE 10

Bicyclic Lactone Diol (formula IIIα: W is 1-pentyl)

Refer to Chart B. The formula-VII triol acid is relactonized by treament in chloroform solution at reflux temperature with pyridine hydrochloride (0.015 g.) for 1hr. The mixture is cooled and concentrated under reduced pressure. The residue is subjected to silica gel chromatography, eluting with methyl acetate-Skillysolve B (80:20) to yield the formula-IIIα title compound.

EXAMPLE 11

Bicyclic Lactone Diol Monopropionate (Formula VI: $R_1$ ethyl and W is 1-pentyl)

Refer to Chart B. The formula-Vα 3S diol diester (Example 5, 0.2 g.) is treated in 3 ml. of methanol with sodium bicarbonate (0.02 g.) and thereafter with sodium carbonate (0.01 g.). The reaction is completed in 15 min. The mixture is acidified with acetic acid, stirred for 0.5 hr., and concentrated under reduced pressure. The residue is taken up in dichloromethane, washed with N. hydrochloric acid, 5% aqueous sodium hydrogen carbonate, and dried over sodium sulfate. Concentration under pressure yields the formula-VI title compound, having $R_f$ 0.42 (TLC on silica gel in ethyl acetate-Skellysolve B (1:1)).

EXAMPLE 12

Endo-6-(1S, 2S-dihydroxyheptyl)-exo-3-hydroxybicyclo[3.1.0]hexan-exo-2-acetic Acid, γ-Lactone (Formula XII: ∼ is alpha and W is 1-pentyl)

Refer to Chart C.

a. Endo-6-(1S, 2R-dihydroxyheptyl)-exo-3-hydroxybicyclo[3.1.0]hexan-exo-2-acetic acid, γ-lactone (the more polar erythro glycol of Example 16 of U.S. Pat. No. 3,711,515, 14.4 g.) in 400 ml. of diethyl ether and 200 ml. of pyridine is treated at 5° C. with p-toluenesulfonyl chloride (42.8 g.) and maintained thereafter at −6° C. for 6.5 days, thereby forming the 2R monotosylate.

b. To the above reaction mixture is added acetic anhydride (46.5 g.) slowly with stirring and the mixture is maintained thereafter at −6° C. for about 16 hr. The mixture is then added to 1 liter of ice water, stirred for 30 min., acidified to pH 4 with phosphoric acid, and extracted several times with benzene. The organic phase is washed with water, dried over magnesium sulfate, and concentrated under reduced pressure to the formula-X compound.

c. One-half of the product of (b) (16.3 g.) is dissolved in 100 ml. of 90% acetic acid and treated with sodium acetate (13 g.). The mixture is heated at 90° C. for 2.5 hr., cooled to about 25° C., neutralized with aqueous saturated sodium carbonate solution to pH 6, and then extracted with dichloromethane several times. The organic phase is dried and concentrated to yield the formula-XI mixed monoesters (10.7 g.), an oil.

d. The product of step (c) is dissolved in 20 ml. of methanol and 20 ml. of aqueous 2N. sodium hydroxide and stirred at about 25° C. under nitrogen for 3 hr. The solution is partially concentrated under reduced pressure and extracted with dichloromethane to remove neutral compounds. The remaining reaction mixture is then acidified to pH 3 with phosphoric acid, with cooling, and stirred until relactonization is complete. The mixture is saturated with sodium chloride and extracted four times with ethyl acetate. The combined organic phase is washed with 5% aqueous sodium bicarbonate to pH 8, dried over calcium sulfate, and concentrated under reduced pressure to the formula-XII title compound, 5.5 g. (76% yield).

EXAMPLE 13

Endo-6-(1R, 2S-dihydroxyheptyl)-exo-3-hydroxybicyclo[3.1.0]hexan-exo-2-acetic Acid, γ-Lactone (Formula XII: ∼ is beta and W is 1-pentyl)

This example illutrates the use of an epoxide intermediate.

a. Following the procedure of Example 12, step (a), endo-6-(1S, 2R-dihydroxyheptyl)-exo-3-hydroxybicyclo[3.1.0]hexan -exo-2-acetic acid, γ-lactone (13.8 g.), is reacted with p-toluenesulfonyl chloride to form the 2R-monotosylate. The mixture is concentrated to removed ether and the residual mixture is then added to 600 ml. of ice water, stirred for 15 min., acidified to pH 4 with phosphoric acid, and separated from a gummy residue. The solution and the gummy residue are extracted separately with ethyl acetate, which extracts are then combined, dried over magnesium sulfate, and concentrated. The oily residue is crystallized from ethyl acetate-Skellysolve B as the monotosylate, 13 g. The product is subjected to silica gel chromatography, eluting with 50–70% ethyl acetate in Skellysolve B, to yield 9.4 g. of crystalline product, m.p. 116°–118° C.

b. The epoxide is next prepared as follows. To a solution of the monotosylate of step a (0.26 g.) in 7 ml. of methanol, cooled to 5° C., is added sodium methoxide (0.035 g.). After the reaction is complete as shown by TLC, in approximately 15 min., the mixture is added to 20 g. ice and 40 ml. of 10% buffer pH 6.8. The mixture is extracted with dichloromethane several times and the organic phase is dried over magnesium sulfate and concentrated under reduced pressure. There is obtained endo-6-(1S, 2S-epoxyheptyl)-exo-3-hydroxybicyclo[3.1.0]hexan-exo-2-acetic acid, γ-lactone, 0.17 g., having $R_f$ 0.56 (TLC on silica gel in ethyl acetate-Skellysolve B (1:1)).

c. The epoxide is then opened as follows. A mixture of the above epoxide (0.5 g.), 3 ml. of 20% aqueous sodium formate solution, and 0.13 ml. of formic acid in 7 ml. of tetrahydrofuran is stirred at about 25° C. for 32 hr. Then 0.1 ml. of formic acid is added and stirring continued. At 73 hr. there is added 0.1 g. of potassium hydrogen carbonate and 2 ml. of buffer pH 6.8. The mixture is concentrated under reduced pressure and the residue is partitioned between 20 ml. of water and 20 ml. of dichloromethane. The organic phase is dried and concentrated. The residue is stirred in 6 ml. of methanol with potassium hydrogen carbonate (0.06 g.) until no formates were left as shown by TLC. After 1.75 hr., there is added 2 ml. of phosphate buffer pH 6.8 and the mixture concentrated under reduced pressure. The residue is partitioned between 20 ml. of water and 20 ml. of dichloromethane. The organic phase is dried over sodium sulfate, and concentrated to a product containing about 75% of the title compound, the balance being the corresponding 1S, 2S glycol and a small amount of the formula-IIIα diol.

I claim:

1. A process for preparing an optically active bicyclic lactone diol of the formula

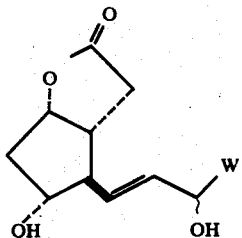

or a racemic compound of that formula and the mirror image thereof, wherein W is 1-pentyl, cis 1-pent-2-enyl, or 1-pent-2-ynyl, and ~ indicated attachment of the hydroxyl to the side chain in alpha or beta configuration, which comprises the steps of a. reacting an optically active tricyclic lactone glycol of the formula

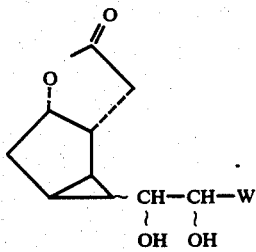

or a racemic compound of that formula and the mirror image thereof, wherein W is as defined above and ~ indicates attachment of the moiety to the cyclopropane ring in exo and endo configuration and to the side chain in alpha or beta configuration, and an ortho ester of the formula

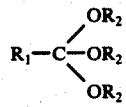

wherein $R_1$ is hydrogen, alkyl of 1 to 19 carbon atoms, inclusive, or aralkyl of 7 to 12 carbon atoms, inclusive, substituted with zero to 3 halo atoms; and $R_2$ is methyl or ethyl in the presence of an acid catalyst, to form an optically active cyclic ortho ester of the formula

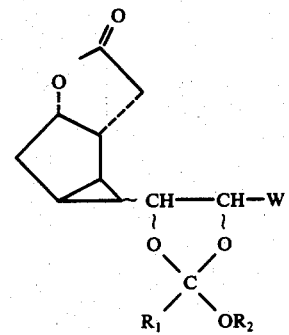

or a racemic compound of that formula and the mirror image thereof, wherein $R_1$, $R_2$, W, and ~ are as defined above;

b. reacting said cyclic ortho ester with anhydrous formic acid to form an optically active diol diester of the formula

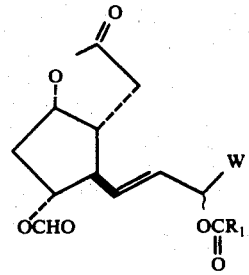

or a racemic compound of that formula and the mirror image thereof, wherein $R_1$, W, and ~ are as defined above; and c. replacing the acyl groups of said diol diester with hydrogen by alcoholysis in the presence of a base.

2. A process according to claim 1 wherein ~ in the formula of the product diol is in the alpha configuration, and, in the formula of the starting glycol, and ~ OH attached to —CH—W is in the alpha configuration.

3. A process according to claim 1 wherein $R_1$ is hydrogen or alky of 1 to 7 carbon atoms, inclusive.

4. A process according to claim 1 wherein $R_1$ is hydrogen or alkyl of 1 to 4 carbon atoms, inclusive.

5. A process according to claim 1 wherein $R_1$ is hydrogen, methyl, or ethyl, and W is 1-pentyl.

6. A process according to claim 5 wherein $R_1$ is ethyl.

* * * * *